United States Patent [19]
Sweet

[11] Patent Number: 5,147,916
[45] Date of Patent: Sep. 15, 1992

[54] HOT-MELT SILICONE PRESSURE SENSITIVE ADHESIVE COMPOSITION AND RELATED METHODS AND ARTICLES

[75] Inventor: Randall P. Sweet, Midland, Mich.

[73] Assignee: Dow Corning Corporation, Midland, Mich.

[21] Appl. No.: 485,015

[22] Filed: Feb. 21, 1990

[51] Int. Cl.$^5$ ............................................. C08K 5/24
[52] U.S. Cl. ................................. 524/266; 524/490; 524/476; 524/268
[58] Field of Search ............... 524/490, 476, 266, 268

[56] References Cited

U.S. PATENT DOCUMENTS

| | | | |
|---|---|---|---|
| 3,954,692 | 5/1976 | Downey | 260/33.6 AQ |
| 4,001,167 | 1/1977 | Tungseth et al. | 260/33.6 AQ |
| 4,032,492 | 7/1977 | Englund et al. | 524/476 |
| 4,038,346 | 7/1977 | Feeney | 260/887 |
| 4,064,094 | 12/1977 | Downey | 260/32.8 A |
| 4,089,824 | 5/1978 | Bronstert et al. | 260/27 BB |
| 4,136,699 | 1/1979 | Collins et al. | 525/95 |
| 4,253,460 | 3/1981 | Chen et al. | 128/283 |
| 4,335,026 | 6/1982 | Balinth | 524/271 |
| 4,395,443 | 7/1983 | Shimizu et al. | 524/490 |
| 4,427,737 | 1/1984 | Cilento et al. | 428/315.7 |
| 4,551,490 | 11/1985 | Doyle et al. | 524/22 |
| 4,613,640 | 9/1986 | Deisler et al. | 524/490 |
| 4,634,629 | 1/1987 | Inaba et al. | 428/343 |
| 4,680,333 | 7/1987 | Davis | 524/394 |
| 4,699,816 | 10/1987 | Galli | 428/40 |
| 4,714,655 | 12/1987 | Bordoloi et al. | 428/345 |
| 4,728,572 | 3/1988 | Davis | 428/355 |
| 4,793,337 | 12/1988 | Freeman et al. | 428/156 |
| 4,814,168 | 3/1989 | Sablotsky et al. | 424/78 |
| 4,865,920 | 9/1989 | Sweet | 428/447 |
| 4,882,377 | 11/1989 | Sweet et al. | 524/267 |

OTHER PUBLICATIONS

"Customizing Silicone Adhesives for Transdermal Drug Delivery Systems", by William R. Pfister, reprinted from Pharmaceutical Technology, Mar. 1989 (10 pages).

*Primary Examiner*—Karen A. Hellender
*Attorney, Agent, or Firm*—Lynn E. Cargill; Susan M. Cornwall

[57] ABSTRACT

Hot-melt silicone pressure sensitive adhesive composition, methods of using the composition, article made using the composition, and methods of making articles using the composition. The hot-melt silicone pressure sensitive adhesive composition includes a mixture of (i) a silicone resin, (ii) a silicone fluid, and (iii) from about 0.5 to about 10 weight percent, based on the total weight of the silicone resin and the silicone fluid, of a non-flammable hydrocarbon having a weight-average molecular weight of from about 300 to about 1500 as measured by gel permeation chromatography calibrated with narrow distribution polydimethylsiloxane standards.

6 Claims, No Drawings

HOT-MELT SILICONE PRESSURE SENSITIVE ADHESIVE COMPOSITION AND RELATED METHODS AND ARTICLES

TECHNICAL FIELD

The present invention relates to hot-melt silicone pressure sensitive adhesive compositions and related methods and articles.

BACKGROUND OF THE INVENTION

A pressure sensitive adhesive, generally, is a material which adheres to a surface with slight pressure and releases from the surface with negligible transfer of the material to the surface. Silicone pressure sensitive adhesives that are known in the art are typically solvent-based adhesives; the solvents are employed primarily to reduce the silicone pressure sensitive adhesive's viscosity to a viscosity which is easily coated onto the substrate of choice, and the solvents are removed after coating. As with any solvent-based pressure sensitive adhesive (PSA), special precautions must be taken to contain and avoid environmental exposure of the solvents and avoid flammable and explosive conditions since many of the solvents used are flammable.

Hot-melt pressure sensitive adhesives are those adhesives, which upon heating, melt to viscosities suitable for coating, but when cooled are generally in a flowless state. The advantages of hot-melt PSA's relative to solvent-based PSA's are known. Namely, the advantages of hot-melt PSA's are that they (1) do not require removal and containment of solvents, (2) do not require special precautions to avoid fires due to the presence flammable solvents, (3) make available coating processes other than those commonly used with solvent-based PSA's and (4) are more easily coated into thick thicknesses with minimal bubbling which often results with solvent-containing PSA's. In addition, solventless PSA's have the advantage of not containing solvents which sometimes interfere with the addition of other ingredients to the PSA.

Silicone pressure sensitive adhesives have been found to be preferred over other types of PSA's in many applications, especially in the medical area. For example, silicone pressure sensitive adhesives, due to the fact that they are acceptable for topical use, have found use in transdermal drug delivery applications which involve the adherence of a drug-containing patch to a patient's skin.

U.S. Pat. No. 4,865,920 to Randall P. Sweet, also the inventor of this invention, discloses a method of making hot-melt silicone pressure sensitive adhesives which have the inherent benefits of being composed of silicone and being a hot-melt PSA. In U.S. Pat. No. 4,865,920, the hot-melt silicone pressure adhesive composition consists of (i) a silicone resin, (ii) a silicone fluid, and (iii) 1 to 10 weight percent, based on the total weight of the silicone resin and silicone fluid, of an ester having the formula: R—C(O)OR' wherein R is a monovalent non-flammable hydrocarbon radical having from 2 to 32 carbon atoms and R' is a monovalent non-flammable hydrocarbon radical having from 1 to 14 carbon atoms. Although this silicone pressure sensitive adhesive composition has been found to be highly efficacious, it is desirable to have a hot-melt silicone pressure sensitive adhesive which uses ingredients which are (1) less toxic and more skin-compatible, (2) more available, and (3) less expensive than the aforementioned esters. The higher degree of skin compatibility is desirable especially for dermal applications.

It is also desirable that the new hot-melt silicone pressure sensitive adhesive be capable of being substantially transparent and have controllable adhesion, so that the aggressiveness of adhesion can be tailored to the application. For example, in terms of the transdermal drug delivery patch application, it is desired that the PSA exhibit a suitable adherence to the skin so that it remains adhered for the desired amount of time, but is comfortable to the patient upon removal.

SUMMARY OF THE INVENTION

This invention provides a hot-melt pressure sensitive adhesive composition which possesses the benefits of being a hot-melt adhesive and being formed of materials which are highly acceptable in topical applications. The hot-melt silicone pressure sensitive adhesive compositions of this invention utilize ingredients that are readily available and relatively inexpensive. The invention also provides a means of controlling the pressure sensitive adhesive properties of tack, adhesion, and release of the composition.

The invention fulfills the foregoing needs by providing a hot-melt silicone pressure sensitive adhesive composition comprising a mixture of (i) a silicone resin and (ii) a silicone fluid, said mixture exhibiting tackiness and adhesiveness, said mixture being blended with (iii) from about 0.5 to about 10 weight percent based on the total weight of the silicone resin and the silicone fluid, of at least one non-flammable hydrocarbon having a weight-average molecular weight of from about 300 to about 1500 as measured by gel permeation chromatography calibrated with narrow distribution polydimethylsiloxane standards. The invention also encompasses methods of using the composition and the method of making a hot-melt silicone pressure sensitive adhesive-coated substrate, and methods of making and using the coated substrates.

DETAILED DESCRIPTION OF THE INVENTION

Generally, the hot-melt compositions of the invention are composed of a silicone pressure sensitive adhesive and at least one non-flammable hydrocarbon having a weight-average molecular weight of from about 300 to about 1500 as measured by gel permeation chromatography calibrated with narrow distribution polydimethylsiloxane standards. The components of the hot-melt silicone pressure sensitive adhesive other than the non-flammable hydrocarbon may be selected from various known silicone pressure sensitive adhesives. Typical silicone pressure sensitive adhesives include a volatile organic solvent, such as xylene (which is flammable and requires environmental control), or trichlorotrifluoroethane (which requires environmental control) for reducing the viscosity of the composition to a coatable room-temperature viscosity, and, after coating, the organic solvent is removed by evaporation. The hot-melt silicone pressure sensitive adhesive compositions of this invention do not employ such solvents that are to be removed, but their viscosities are still capable of being reduced to suitable viscosities for coating at elevated temperatures due to the presence of certain non-flammable hydrocarbons.

Optionally, the hot-melt silicone pressure sensitive adhesive compositions of the invention may include a minor amount of filler, such as extending or reinforcing filler. It is usually desired that the filler be present in an amount no greater than about 5 weight % based on the total weight of the silicone resin and the silicone fluid.

One suitable class of pressure sensitive adhesives to be employed in the hot-melt compositions of this invention consists of a mixture of (i) a trimethylsilyl-endblocked polysilicate resin such as a silicone resin consisting of a benzene-soluble resinous copolymer containing silicon-bonded hydroxyl radicals and consisting essentially of triorganosiloxy units of the formula $R_3SiO_{\frac{1}{2}}$ and tetrafunctionalsiloxy units of the formula $SiO_{4/2}$ in a ratio of about 0.6 to 0.9 triorganosiloxy units for each tetrafunctionalsiloxy unit present in the copolymer, wherein each R is a monovalent organic radical independently selected from the group consisting of hydrocarbon radicals of from 1 to 6 inclusive carbon atoms, and (ii) a silanol-endstopped polydiorganosiloxane fluid, e.g. a polydimethylsiloxane fluid. U.S. Pat. No. 2,736,721 to Dexter, et al. and U.S. Pat. No. 2,814,601, to Currie, et al. are hereby incorporated by reference to teach of such or similar pressure sensitive adhesive compositions.

Another class of suitable pressure sensitive adhesives to use with the non-flammable hydrocarbons according to the invention, is that of those similar to that of U.S. Pat. No. 2,857,356, to Goodwin, Jr., which is hereby incorporated by reference. The Goodwin, Jr. patent teaches of silicone pressure sensitive adhesives which consist of a mixture of ingredients comprising (i) a cohydrolysis product of a trialkyl hydrolyzable silane and alkyl silicate, wherein the cohydrolysis product contains a plurality of silicon-bonded hydroxy groups, and (ii) a linear, high viscosity organopolysiloxane fluid containing silicon-bonded hydroxy groups.

The silicone resin (i) and the silicone fluid (ii) may optionally be condensed together according to a procedure such as the procedure described in Canadian Patent 711,756 to Pail, which patent is hereby incorporated by reference. In such a condensation reaction, the silicone resin (i) and the silicone fluid (ii) are mixed together in the presence of a catalytic amount of a silanol condensation catalyst, and then the silicone resin (i) and the silicone fluid (ii) are condensed, for example, by heating under reflux conditions for 1 to 20 hours. Examples of silanol condensation catalysts are primary, secondary, and tertiary amines, carboxylic acids of these amines and quaternary ammonium salts.

Another class of suitable pressure sensitive adhesives to use with the non-flammable hydrocarbons according to the invention are those compositions described in U.S. Pat. Nos. 4,591,622 and 4,584,355 to Blizzard et al., U.S. Pat. No. 4,585,836 to Homan et al., and U.S. Pat. No. 4,655,767 to Woodard et al., which patents are hereby incorporated by reference. Generally, these pressure sensitive adhesives consist of a blend of (i) a silicone resin and (ii) a silicone fluid which are chemically treated so as to reduce the silicon-bonded hydroxyl content of the blend. These adhesives may optionally be condensed as described immediately above prior to the chemical treatment.

Generally speaking, the silicone resin is employed in amounts from about 40 to about 70 parts by weight in the silicone pressure sensitive adhesive, and the silicone fluid is employed from about 30 to about 60 parts by weight, wherein the total parts of the silicone resin and the silicone fluid is 100 parts. It is usually preferred that the silicone resin be employed from about 50 to about 60 parts by weight, and, correspondingly, the silicone fluid is employed from about 40 to about 50 parts by weight, wherein the total parts by weight equals 100.

The silicone pressure sensitive adhesives used in this invention are not considered to be "silicone rubbers" which generally refer to non-tacky vulcanized rubbers. The silicone pressure sensitive adhesives employed in this invention are tacky (or sticky) to the touch and typically adhere to a substrate after mild pressure is applied. The silicone pressure sensitive adhesives may be cured or "rubberized" after being mixed with the non-flammable hydrocarbon as discussed below. However, even after the curing, the silicone pressure sensitive adhesive is tacky. Mineral oil, one of the suitable non-flammable hydrocarbons for this invention, is generally not compatible in the most common type of silicone rubber, which consists of a mixture of a polydimethysiloxane gum, a filler (such as fumed silica or other inorganic, non-resinous material), a crosslinker, and optionally, a catalyst. Surprisingly, however, it was found that mineral oils and petrolatum (another suitable non-flammable hydrocarbon for this invention) are substantially compatible in the silicone pressure sensitive adhesives employed. The compatibility is believed to be due to the fact that the non-flammable hydrocarbon is absorbed into the interstices of the benzene-soluble silicone resin included in the adhesive.

Another difference between the silicone pressure sensitive adhesives and silicone rubber lies in the fact that silicone pressure sensitive adhesives are usually fillerless or contain low amounts, e.g. less than about 5 weight %, of fillers, such as fumed silica or other inorganic reinforcing fillers known in the silicone art. On the other hand, silicone rubbers typically contain about 15-35 weight % filler. Fillers are usually not desired in high quantities in silicone pressure sensitive adhesives, because high quantities often cause the silicone pressure sensitive adhesives to lose tack and adhesiveness and to increase in viscosity, making it more difficult to apply a coating of the silicone pressure sensitive adhesive.

The hot-melt silicone pressure sensitive adhesive compositions of the invention are prepared by merely mixing siloxanes (i) and (ii) with the selected non-flammable hydrocarbon(s). The hot-melt silicone pressure sensitive adhesive compositions are then heated to a coatable viscosity and coated on a substrate. Optionally, the coated compositions may be cured. When the composition is to be cured, the composition may further contain a curing catalyst. It is preferred that such catalysts remain inactive at room temperature and temperatures reached during the hot-melt coating process. Therefore, such catalysts that either become active at temperatures higher than that of the hot-melting temperatures or become active upon exposure to another energy source, e.g. UV light or electron beam radiation, are most suitable.

The process of crosslinking silicone pressure sensitive adhesives is known in the art. For example, see "Silicone Pressure—Sensitive Adhesives" by D. F. Merrill in the *Handbook Of Pressure—Sensitive Adhesive Technology*, edited by D. Satas (Van Nostrand Reinhold, Florence, Ky., 1982), pages 344–352 and "Formulating Silicone Pressure Sensitive Adhesives For Application Performances" by L. A. Sobieski in *Making It Stick in '86, Advances In Pressure—Sensitive Tape Technology*, seminar proceedings (Pressure Sensitive Tape Council, Deerfield, Ill., 1986), pages 1–5, both sources being hereby incorporated by reference.

Appropriate non-flammable hydrocarbons for this invention include those that are entirely liquid and those that are combinations of liquid and solid non-flammable hydrocarbons. Straight-chain, branched, saturated, and C=C unsaturated non-flammable hydrocarbons are possible types of non-flammable hydrocarbons useful in the invention. These non-flammable hydrocarbons are suitable for topical (on animal skin) applications, such as in the case of transdermal drug applications. The non-flammable hydrocarbons used in this invention differ from the esters used in the aforementioned U.S. Pat. No. 4,865,920 not only in that they are relatively more skin-compatible than the esters, but also the non-flammable hydrocarbons vary in their functional mechanism. The esters of the '920 patent are soluble in the silicone fluid phase of the PSA composition, whereas the non-flammable hydrocarbons of this invention are compatible in the resin phase of the PSA composition. Due to the non-flammable hydrocarbon's good compatibility in the PSA compositions, the hot-melt silicone pressure sensitive adhesive compositions exhibit clarity, which is desirable in many end-use applications. The compatibility of the non-flammable hydrocarbons in the silicone pressure sensitive adhesives was a surprising discovery, as the non-flammable hydrocarbons, such as mineral oil and petrolatum are not compatible with polydimethylsiloxanes and not generally compatible with silicone rubbers. It has been found that the described non-flammable hydrocarbons do not bleed to the surface of the hot-melt silicone pressure sensitive adhesive compositions, and therefore, the tack and adhesion characteristics of the silicone pressure sensitive adhesives continue to exist in the presence of the non-flammable hydrocarbon.

Suitable weight-average molecular weight ranges for the non-flammable hydrocarbons of this invention are from about 300 to about 1500, preferably from about 400 to about 1000, as measured by gel permeation chromatography calibrated with narrow distribution polydimethylsiloxane standards. In many cases, it is preferred that the non-flammable hydrocarbon have a weight-average molecular weight between about 400 and 500. In addition to the non-flammable hydrocarbon having the desired weight-average molecular weight, non-flammable hydrocarbons having molecular weights outside of the desired range may be included in the composition. Special considerations must be made, however, if is desired to have a non-flammable composition. In other words, significant amounts of low molecular weight flammable species should be avoided in this instance. Furthermore, non-flammable hydrocarbons in amounts which cause detrimental effects to the hot-melt silicone pressure sensitive adhesive composition to the point of not be useful should be avoided The non-flammable hydrocarbons for the hot-melt silicone pressure sensitive adhesive compositions of the invention are not flammable which affords a safer procedure during application of the hot-melt silicone pressure sensitive adhesive compositions at elevated temperatures. Flammable materials, as the term is used herein, are those materials which are flammable according to the definition provided in United States Code of Federal Regulations (CFR), Title 49, Part 173, Section 115 (49 CFR 173.115). Briefly restated, a flammable liquid means any liquid having a flash point below 100° F., where flash point means the minimum temperature at which a liquid gives off vapor within a test vessel in sufficient concentration to form an ignitable mixture with air near the surface of the liquid. The CFR provides proper testing conditions for measuring flash point. If flammable materials are included in the composition, the coating operation could be done in an inert atmosphere (e.g. nitrogen gas), devoid of combustible gas to avoid fire hazards.

The non-flammable hydrocarbon employed must not boil at the processing temperatures. Typically, temperatures above about 100° C. produce suitable working viscosities with the compositions of this invention, therefore, non-flammable hydrocarbons having boiling points above 100° C. ar preferred.

Examples of suitable non-flammable hydrocarbons include light mineral oil, heavy mineral oil, and petrolatum. Heavy mineral oil is a mixture of liquid hydrocarbons from petrolatum having a boiling point of about 360° C. at 760 mmHg. Heavy mineral oil has a density of about 0.875–0.905, and light mineral oil has a density of about 0.83–0.86. Petrolatum is a colloidal system of non-straight-chain solid hydrocarbons and high-boiling liquid hydrocarbons, in which most of the liquid hydrocarbons are held inside the micelles. Petrolatum has a specific gravity of about 0.820–0.865 at 60° C. with reference to water at 25° C.

Gel permeation chromatography analysis (GPC) was completed on light and heavy mineral oil and petrolatum. The equipment used was a Varion MicroPak TSK H Series GPC analyzer (available from Varion Laboratories) which included a bank of four columns, the columns having pore sizes of $10^6$, $10^5$, $10^4$, and 500 Angstroms. The analyzer was calibrated using narrow distribution (having a 1.1–1.3 polydispersity index) polydimethylsiloxane standards in toluene. The detector was a refractive index detector. A flow rate of 1.500 ml/min, a 50-microliter injection volume, a 1% dilution, and an oven temperature of 45.00° C. was used for testing. The curve fit was linear regression with a Y-intercept of 11.6646100 and a slope of −0.33144190.

Light mineral oil had a bimodal curve indicating species having two distinct molecular weight ranges. Approximately 20 weight percent of the light mineral oil consisted of a molecules having a peak molecular weight of about 27,434, a number-average molecular weight of about 15,907, a weight-average molecular weight of about 53,132, a Z-average molecular weight of about 247,609, and a polydispersity index of about 3.34. The baseline measurements were 15.94 and 31.21 minutes, the summation endpoints were 16.81 to 25.27 minutes, and the relative baseline drift was 0%.

The second species of the light mineral oil, which comprises about 80 weight % of the light mineral oil, had a peak time of 27.14, a peak molecular weight of about 468, a number-average molecular weight of about 354, a weight-average molecular weight of about 443, a Z-average molecular weight of about 523, and a polydispersity index of about 1.25. For the second predominant species, the baseline measurements were 24.75 and 30.12 minutes, the summation endpoints were 25.75 to 29.81 minutes, and the relative baseline drift was 1.1743%.

GPC analysis of heavy mineral oil indicated a peak time of 26.75, a peak molecular weight of about 627, a number-average molecular weight of about 495, a weight-average molecular weight of about 613, a Z-average molecular weight of about 717, and a polydispersity index of about 1.24. The baseline measurements were 23.09 and 30.12 minutes, the summation endpoints were 25.45 to 29.42 minutes, and the relative baseline drift was 2.8725%.

GPC analysis of petrolatum indicated a peak time of 26.41, a peak molecular weight of about 814, a number-average molecular weight of about 670, a weight-average molecular weight of about 902, a Z-average molecular weight of about 1201, and a polydispersity index of about 1.35. The baseline measurements were 20.21 and 29.90 minutes, the summation endpoints were 24.23 to 29.16 minutes, and the relative baseline drift was 0.7423%.

When the hot-melt silicone pressure sensitive adhesive composition is to be used in medical applications, USP (United States Pharmacopeia) grades are preferred. Light mineral oil is preferred over the heavy mineral oil and petrolatum in this invention, as more dramatic reductions in the viscosity has been found with the light mineral oil as compared to the heavy mineral oil and petrolatum.

The non-flammable hydrocarbons may be employed in amounts of about 0.5 to 10 weight percent based on the total weight of the silicone resin and the silicone fluid. Preferably, the non-flammable hydrocarbon is employed at less than about 5 weight percent. At the higher amounts, especially with low molecular weight non-flammable hydrocarbons, the hot-melt silicone pressure sensitive adhesive composition may be too flowable at room temperature which is undesirable for most PSA applications. This problem may be overcome, however, by curing the PSA after coating.

The hot-melt silicone pressure sensitive adhesive compositions of this invention may be made by mixing the ingredients in any order. Reaction or treatment of the ingredients, e.g., condensing according to the procedure of the previously-mentioned Pail patent or chemically treating according to the previously-mentioned Blizzard et al., etc. patents may require completion prior to the addition of the non-flammable hydrocarbon.

The inclusion of the non-flammable hydrocarbon allows the hot-melt silicone pressure sensitive adhesive composition to decrease in viscosity with elevated temperatures to a suitable viscosity for coating a substrate without the use of solvents that must be removed. Suitable viscosities for hot-melt processing are about 20,000–40,000 centipoise, and, more typically, 30,000–40,000 centipoise.

When using the hot-melt silicone pressure sensitive adhesive compositions of this invention to coat a substrate, the method comprises the steps of (a) heating the hot-melt silicone pressure sensitive adhesive composition to a coatable temperature above 25° C., (b) coating the heated hot-melt silicone pressure sensitive adhesive composition on the substrate, and (c) cooling the coated hot-melt silicone pressure sensitive adhesive composition until it is in a generally non-flowing state. Typically, heating the hot-melt silicone pressure sensitive adhesive compositions of this invention to temperatures of about 100° C. or more (more typically about 150° C.) results in suitable viscosities less than 40,000 centipoise. These coatable temperatures are low enough so that decomposition of the composition does not occur. Lower temperatures may result in coatable viscosities depending on the coating equipment used, the desired end product, and the composition of the hot-melt silicone pressure sensitive adhesive composition. For example, the thicker the layer of pressure sensitive adhesive desired, the higher the coating viscosity can be.

When the hot-melt silicone pressure sensitive adhesive compositions are applied to a backing or substrate, this procedure may be accomplished by using any conventional means, such as, roller coating, dip coating, extrusion, knife coating, or spray coating.

The hot-melt silicone pressure sensitive adhesive compositions of the invention will adhere to many substrates, such as paper, cloth, glass cloth, silicone rubber, polyethylene, polyethylene terephthalate, polytetrafluoroethylene, glass, wood, metals, and skin. Therefore, there are many uses for the hot-melt silicone pressure sensitive adhesive compositions of this invention. Depending on the desired use, it may be desirable to apply adhesion promoters on the substrate surface upon which the hot-melt silicone pressure sensitive adhesive composition will be placed.

The hot-melt silicone pressure sensitive adhesive compositions of this invention are especially suitable for assisting in delivering a bioactive agent, such as a drug, to a bioactive-agent accepting substrate, such as a patient's skin. The hot-melt silicone pressure sensitive adhesive composition of this invention may be employed in two types of bioactive agent delivery modes. One mode is by incorporating the bioactive agent in the hot-melt silicone pressure sensitive adhesive composition which is thereafter attached to the substrate to commence delivery. The second mode of delivery is by attaching a membrane of the hot-melt silicone pressure sensitive adhesive composition to the substrate and, then, contacting a reservoir of a bioactive agent to the attached membrane. The bioactive agent may then pass from the reservoir through the attached membrane and to the substrate for absorption. This second mode of delivery is a common transdermal drug delivery technique. For this mode, a bioactive agent delivery device may be made which includes (a) a container, (b) a bioactive agent contained in the container, and (c) a hot-melt silicone pressure sensitive adhesive composition of this invention on the container for providing a means for adhering the container to the bioactive-agent accepting substrate.

In addition, the hot-melt silicone pressure sensitive adhesive compositions of this invention have the potential advantage, when used in transdermal drug delivery applications, to provide additional benefits in terms of providing an improved control of permeation rates of the drug through the skin and skin softening due to the presence of the non-flammable hydrocarbon.

The following examples of the invention are meant to be illustrative only and should not be construed as limiting the invention which is properly delineated in the appended claims. In the following examples, all parts and percentages are by weight unless otherwise specified.

"N.V.C." (Nonvolatile Content) of a resin, as given below, was determined by mixing 1.5 g of the resin with 0.75 g. of a 100 cSt. viscosity trimethylsiloxy-endblocked polydimethylsiloxane (PDMS) fluid in an aluminum foil dish, 60 mm in diameter and 15 mm deep, and heating the sample for 2 hours at 150° C. in an air-circulating oven. The heated sample was then cooled to room temperature and reweighed to determine the weight of the nonvolatile material (w). The N.V.C., in percent, is equal to 100×w/1.5.

For the following examples, Resin A-1 is a xylene solution of a resinous copolymeric siloxane prepared from 45 parts of sodium silicate (41.6° Be) and 20 parts of Me$_3$SiCl (Me=CH$_3$) according to the method of U.S. Pat. No. 2,676,182 to Daudt, et al., which is hereby incorporated by reference, and contains $Me_3SiO_{\frac{1}{2}}$ units and $SiO_{4/2}$ units in a ratio of approximately 0.75:1.0, and has a N.V.C. typically about 69–71%, an acid number in the range of 0.3 to 1.4, a viscosity in the range of 10–14 centipoise at 25° C. at 60% N.V.C. in xylene solution, and a silicon-bonded hydroxyl content of about 2.5 weight percent based on a 100% N.V.C.

Resin A-2 is devolatilized Resin A-1 (100% nonvolatile content).

PDMS Fluid A is a homogeneous mixture of a hydroxyl-endblocked polydimethylsiloxane having a number-average molecular weight of approximately 40,000 and minor amounts of cyclic polydimethylsiloxane having degrees of polymerization between 4 and 30, the mixture having a viscosity between 12,000 and 15,000 centipoise as measured using a Brookfield Viscometer Model HAF with spindle #3 at 10 RPM's.

PSA A was prepared by homogeneously mixing 24.1 parts by weight of Resin A-2, 39.8 parts by weight xylene, and 36.1 parts by weigh PDMS Fluid A. The mixture was then heated to 100° C. and anhydrous ammonia was passed through the mixture at a rate of 11 ml/min/lb of non-volatile component of the mixture for 2 hours. To endcap the mixture, hexamethyldisilazane was then admixed at a 3:1 mole ratio of endblocking triorganosilyl to total silicon-bonded hydroxyl radicals present in the resin copolymer and polydiorganosiloxane, and the mixture was allowed to react for 3 hours at 95°–100° C. The mixture was then heated to 140° C. and maintained at 140° C. under reflux conditions for 3 hours to remove condensation water. The mixture was then stripped to greater than 90% nonvolatile content.

PSA B is a pressure sensitive adhesive composition prepared by homogeneously mixing 60 parts of Resin A-1, 40 parts of PDMS Fluid A, and a portion of 2.4 parts of ammonium carbonate, heating the mixture to 100° C. and maintaining the temperature at 100° C. for 1 hour. Then the remaining portion of the 2.4 parts ammonium carbonate were added to the mixture, and mixing continued for another hour at 100° C. The mixture was then stripped for 16 hours at 100° C. to remove the volatile components. PSA B cooled to room temperature had (1) a specific gravity of 1.085–1.115, (2) a N.V.C. of at least 98.8% where N.V.C. is defined as above except that a 1 g. sample was used and the temperature of the oven was 177° C., (3) a plasticity of $150-200\times10^{-3}$ inches as measured after a 24 hour rest and after force was applied on a 2 gram specimen for 3 minutes +/− 5 seconds using ASTM D926, and, (4) when dispersed in trichlorotrifluoroethane to an N.V.C. of 18.5%, the adhesive peel measured at least 1600 g.

PSA C was prepared by homogeneously mixing 26.74 parts of a hydroxy-endblocked polydimethylsiloxane gum having a plasticity between 47 and 60 mils, 30.14 parts Resin A-2, 39.58 parts xylene, 3.40 parts isopropanol, and 0.14 parts of a mixture consisting of 9% tetramethylguanidine, 9% 2-ethyl hexoic acid, and 82% xylene. The plasticity of the gum was measured at room temperature and after force was applied on a 4.2 gram specimen for 3 minutes +/− 5 seconds using ASTM D926. The homogeneous mixture was then stripped to remove the volatile components.

EXAMPLES 1–11

In Examples 2–10, 12–14, and 16–18, hot-melt silicone pressure sensitive adhesive compositions were prepared by mixing the compositions indicated in Table 1 at about 100°–150° C. until homogeneously mixed and then allowing the mixture to cool to room temperature. Examples 1, 11, and 15 are provided to show the properties of the various silicone pressure sensitive adhesives without the added non-flammable hydrocarbon.

TABLE 1

| Example # | PSA Type Employed | Fluid hydrocarbon Employed | Weight % Fluid hydrocarbon Employed* |
|---|---|---|---|
| 1 | PSA A | none | 0 |
| 2 | PSA A | light mineral oil | 1 |
| 3 | PSA A | light mineral oil | 5 |
| 4 | PSA A | light mineral oil | 10 |
| 5 | PSA A | heavy mineral oil | 1 |
| 6 | PSA A | heavy mineral oil | 5 |
| 7 | PSA A | heavy mineral oil | 10 |
| 8 | PSA A | petrolatum | 1 |
| 9 | PSA A | petrolatum | 5 |
| 10 | PSA A | petrolatum | 10 |
| 11 | PSA B | none | 0 |
| 12 | PSA B | light mineral oil | 5 |
| 13 | PSA B | heavy mineral oil | 5 |
| 14 | PSA B | petrolatum | 5 |
| 15 | PSA C | none | 0 |
| 16 | PSA C | light mineral oil | 5 |
| 17 | PSA C | heavy mineral oil | 5 |
| 18 | PSA C | petrolatum | 5 |

*Based on the total weight of the silicone fluid and silicone resin in the PSA composition.

dynamic viscosities (n*) and elastic storage moduli (G') were measured using a Visco-Elastic Tester available from Rheometrics, Piscataway, N.J., and running a temperature sweep on 10 gram samples and operating the tester at a frequency of 10 rad/sec and a 1% strain using a 50 mm cup and plate.

Elastic storage modulus is directly related to die swell and elastic memory. The higher the die swell, the smaller the size of an orifice required for a given coating thickness. Therefore, the lower the elastic storage modulus, the better, as it is then easier to coat onto a substrate. Tests similar to those run in these examples are described in ASTM 4065-82. The viscosities and elastic storage moduli are given in Table 2 and 3, respectively. For comparative purposes, the viscosities and elastic storage moduli of PSA A, B, and C are given in Tables 2 and 3 as Examples 1, 11, and 15, respectively.

TABLE 2

| | Dynamic Viscosity (poise) | | |
|---|---|---|---|
| Example # | 30° C.* | 100° C.* | 200° C.* |
| 1 | 563,700 | 45,420 | 1,161 |
| 2 | 445,200 | 20,250 | 768 |
| 3 | 32,850 | 3,023 | 199 |
| 4 | 6,935 | 889 | 96 |
| 5 | 463,700 | 19,410 | 814 |
| 6 | 66,090 | 4,257 | 269 |
| 7 | 23,670 | 1,280 | 92 |
| 8 | 125,200 | 22,460 | 877 |
| 9 | 206,300 | 5,684 | 253 |
| 10 | 133,300 | 3,477 | 133 |
| 11 | 591,400 | 78,470 | 1,563 |
| 12 | 87,320 | 6,806 | 500 |
| 13 | 174,500 | 9,785 | 678 |

TABLE 2-continued

| Example # | Dynamic Viscosity (poise) 30° C.* | 100° C.* | 200° C.* |
|---|---|---|---|
| 14 | 356,400 | 12,750 | 705 |
| 15 | 399,000 | 50,560 | 10,730 |
| 16 | 63,920 | 22,410 | 6,184 |
| 17 | 82,800 | 25,560 | 7,391 |
| 18 | 162,500 | 28,240 | 6,620 |

*Temperatures are approximate. Actual temperatures ranged from 29 to 30 for the 30° C. column, from 95 to 100 for the 100° C. column, and from 195 to 200 for the 200° C. column.

TABLE 3

| Example # | Elastic Storage Modulus dynes/cm² 30° C.* | 100° C.* | 200° C.* |
|---|---|---|---|
| 1 | 5,570,000 | 225,200 | 3,149 |
| 2 | 4,114,000 | 97,770 | 1,702 |
| 3 | 167,100 | 11,410 | 237 |
| 4 | 34,110 | 2,379 | 105 |
| 5 | 4,348,000 | 94,220 | 1,825 |
| 6 | 350,900 | 17,900 | 765 |
| 7 | 123,000 | 3,329 | — |
| 8 | 1,014,000 | 108,600 | 1,791 |
| 9 | 1,440,000 | 25,530 | 376 |
| 10 | 825,400 | 14,750 | 124 |
| 11 | 5,889,000 | 498,600 | 7,672 |
| 12 | 567,800 | 38,350 | 1,548 |
| 13 | 1,283,000 | 57,140 | 2,159 |
| 14 | 3,172,000 | 76,800 | 2,324 |
| 15 | 3,752,000 | 429,000 | 72,340 |
| 16 | 545,500 | 181,400 | 35,090 |
| 17 | 694,700 | 210,900 | 43,100 |
| 18 | 1,362,000 | 236,700 | 38,990 |

*Temperatures are approximate. Actual temperatures ranged from 29 to 30 for the 30° C. column, from 95 to 100 for the 100° C. column, and from 195 to 200 for the 200° C. column.

Tapes were prepared from the hot-melt silicone pressure sensitive adhesive compositions of these examples to measure adhesion and release values. The compositions were casted to a 1 or 2 mil thickness onto one-inch wide strips of SCOTCH-PAK 1022 Release Liner, a polyester film coated with a release coating available from the 3M Company, St. Paul, Minn., using a hot melt coater manufactured by Bushman Corporation, Kirtland, Ohio, operated at a temperature of about 150° C. After coating, a one-inch wide strip of MYLAR polyester film was adhered to each casted sample with a 4 lb. roller.

The release values were obtained by stripping the tape from the SCOTCH-PAK 1022 Release Liner at a rate of 40 inches/minutes at an angle of 180° while attached to a tensile testing machine, with the results being expressed in grams per centimeter. An average value over the entire length of the liner was recorded.

The tapes (1 or 2 mil thick hot-melt pressure sensitive adhesive composition on MYLAR) were then each adhered to a stainless steel panel with a 4 lb. roller and allowed to rest for 15 minutes. The adhesion measurements were obtained by stripping each tape from the panel at a rate of 12 inches/minute at an angle of 180° while attached to a tensile testing machine, with the results expressed in grams per centimeter.

All of the compositions were tacky to the touch. The adhesion and release values are given in Table 4. For comparative purposes, the adhesion and release values of PSA A, B, and C are given in Table 4 as Examples 1, 11 and 15, respectively.

TABLE 4

| Example # | Coating Thickness (mils) | Release g/cm | Adhesion To Stainless Steel g/cm |
|---|---|---|---|
| 1 | 2 | 2.1 | 723 |
| 2 | 1 | 2.9 | 513 |
| 3 | 2 | 16.5 | 553 |
| 4 | 1 | 11.5 | 107 |
| 5 | 1 | 2.2 | 609 |
| 6 | 2 | 18.0 | 562 |
| 7 | 2 | 12.0 | 91 |
| 8 | 1 | 2.0 | 541 |
| 9 | 2 | 8.1 | 320 |
| 10 | 1 | 9.3 | 169 |
| 11 | 2 | 2.8 | 721 |
| 12 | 1 | 9.1 | 296 |
| 13 | 1 | 9.8 | 424 |
| 14 | 1 | 6.3 | 344 |
| 15 | 2 | 8.4 | 674 |
| 16 | 1 | 6.0 | 223 |
| 17 | 1 | 6.3 | 228 |
| 18 | 1 | 5.9 | 309 |

These and other variations of the present invention may be made which fall within the scope of the appended claims even though such variations were not specifically discussed above.

That which is claimed is:

1. A hot-melt silicone pressure sensitive adhesive composition having a flashpoint below 100° F., comprising a mixture of
   (i) from about 40 to about 70 parts by weight of a trimethylsilyl-endblocked benzene-soluble resinous copolymer containing silicon-bonded hydroxyl radicals and consisting essentially of triorganosiloxy units of the formula $R_3SiO_{\frac{1}{2}}$ and a tetrafunctional siloxy units of the formula $SiO_{4/2}$ in a ratio of about 0.6 to 0.9 triorganosiloxy units for each tetrafunctional siloxy unit present in the copolymer, wherein R is a monovalent organic radical independently selected from the group consisting of hydrocarbon radicals of from 1 to 6 inclusive carbon atoms and
   (ii) from about 30 to about 60 parts by weight of a silanol-endstopped polydimethylsiloxane fluid, wherein the total parts by weight of the resinous copolymer and the polydimethylsiloxane fluid equals 100 parts, said mixture being blended with
   (iii) from about 0.5 to about 10 weight percent, based on the total weight of the resinous copolymer and polydimethylsiloxane fluid, of a hydrocarbon selected from the group consisting of light mineral oil, heavy mineral oil, and mixtures thereof.

2. The hot-melt silicone pressure sensitive adhesive composition of claim 1, wherein said resinous copolymer is employed in an amount from about 50 to about 60 parts by weight, and said polydimethylsiloxane fluid is employed in an amount from about 40 to about 50 parts by weight, wherein the total parts of the resinous copolymer and the polydimethylsiloxane fluid equal 100.

3. The hot-melt silicone pressure sensitive adhesive composition as claimed in claim 1, wherein said hydrocarbon is employed from about 0.5 to about 5 weight percent based on the total weight of said resinous copolymer and said polydimethylsiloxane fluid.

4. The hot-melt silicone pressure sensitive adhesive composition as claim din claim 1, wherein the hot-melt silicone pressure sensitive adhesive composition contains less than about 5 weight % of an inorganic filler.

5. The hot-melt silicone pressure sensitive adhesive composition of claim 1, wherein the hot-melt silicone pressure sensitive adhesive composition is fillerless.

6. The hot-melt silicone pressure sensitive adhesive of claim 1, further comprising a bioactive agent.

* * * * *

UNITED STATES PATENT AND TRADEMARK OFFICE
CERTIFICATE OF CORRECTION

PATENT NO. : 5,147,916

DATED : September 15, 1992

INVENTOR(S) : Randall P. Sweet

It is certified that error appears in the above-identified patent and that said Letters Patent is hereby corrected as shown below:

Column 12, line 26, delete "below", and insert therefor --of at least--.

Signed and Sealed this

Thirtieth Day of November, 1993

Attest:

BRUCE LEHMAN

Attesting Officer

Commissioner of Patents and Trademarks